(12) United States Patent
Marchitto et al.

(10) Patent No.: US 8,014,855 B2
(45) Date of Patent: Sep. 6, 2011

(54) FEEDBACK CONTROL DEVICE FOR TRANSCUTANEOUS DRUG DELIVERY AND USES THEREFOR

(75) Inventors: Kevin S. Marchitto, Golden, CO (US); Stephen T. Flock, Arvada, CO (US)

(73) Assignee: Rocky Mountain Biosystems, Inc., Golden, CO (US)

( * ) Notice: Subject to any disclaimer, the term of this patent is extended or adjusted under 35 U.S.C. 154(b) by 105 days.

(21) Appl. No.: 12/321,885

(22) Filed: Jan. 27, 2009

(65) Prior Publication Data
US 2009/0143715 A1    Jun. 4, 2009

Related U.S. Application Data

(62) Division of application No. 10/422,372, filed on Apr. 24, 2003, now Pat. No. 7,483,736.

(60) Provisional application No. 60/375,287, filed on Apr. 24, 2002.

(51) Int. Cl.
*A61N 1/30*      (2006.01)

(52) U.S. Cl. ........................................... 604/20
(58) Field of Classification Search .............. 604/19–22, 604/113, 114, 890.1, 891.1, 892.1, 65–67; 606/32–50
See application file for complete search history.

(56) References Cited

U.S. PATENT DOCUMENTS

| | | | | |
|---|---|---|---|---|
| 4,713,050 A | * | 12/1987 | Sibalis | 604/20 |
| 5,162,042 A | * | 11/1992 | Gyory et al. | 604/20 |
| 5,693,024 A | * | 12/1997 | Flower | 604/20 |
| 6,477,410 B1 | * | 11/2002 | Henley et al. | 604/20 |

* cited by examiner

*Primary Examiner* — Manuel A Mendez
(74) *Attorney, Agent, or Firm* — Benjamin Aaron Adler

(57) ABSTRACT

Provided herein is a device for altering a biological membrane in an individual comprising a means for delivering energy to the surface of the biological membrane, a means for monitoring a physiological state of the biological membrane during delivery of said energy, a means for modulating delivery of the energy to the biological membrane where the modulating is in response to a change in the monitored physiological state. Also provided is a device to control the permeation of substance across a biological membrane and methods for use of these devices.

17 Claims, 1 Drawing Sheet

FEEDBACK CONTROL DEVICE FOR TRANSCUTANEOUS DRUG DELIVERY AND USES THEREFOR

CROSS-REFERENCE TO RELATED APPLICATION

This is a divisional application of non-provisional application U.S. Ser. No. 10/422,372, filed Apr. 24, 2003, now U.S. Pat. No. 7,483,736 which claims benefit of provisional application U.S. Ser. No. 60/375,287, filed Apr. 24, 2002, the entirety of which is hereby incorporated by reference.

BACKGROUND OF THE INVENTION

1. Field of the Invention

The present invention relates generally to the fields of biomedical physics and drug delivery. More specifically, the present invention provides feedback devices and methods for controlling the alteration of biological membranes and the permeation of substances across biological membranes.

2. Description of the Related Art

Various methods have been used for facilitating the delivery of compounds across the skin and other membranes. Iontophoresis uses an electric current to increase the permeation rate of charged molecules. However, iontophoresis is dependent on charge density of the molecule and has further been known to cause burning in patients. Use of ultrasound has also been tested whereby application of ultrasonic energy to the skin results in a transient alteration of the skin, which leads to an increased permeability to substances. Electromagnetic energy produced by lasers may be used to ablate the stratum corneum in order to make the skin more permeable to pharmaceutical substances (see U.S. Pat. No. 4,775,361). Impulse transients generated by lasers or by mechanical means may be used to make alterations in epithelial layers that result in improved permeation of compounds (see U.S. Pat. No. 5,614,502).

In general, permeation of drugs through the skin occurs at a very slow rate, if at all. The primary rate limiting step in this process is the passage of these compounds through the outermost layer of skin, called the stratum corneum. The stratum corneum is a very thin layer of dead cells that acts as an impermeable layer to matter on either side of this layer. The stratum corneum primarily provides the skin's barrier function. It has long been recognized that loss or alteration of the stratum corneum results in increased permeability to many substances; materials can more easily diffuse into or out of the skin. It has also been demonstrated that electromagnetic energy induced alterations of the stratum corneum result in increased permeability to substances U.S. Pat. Nos. 6,315, 722, 6,251,100, 6,056,738 and 5,643,252. Alternatively, compounds referred to as permeation enhancers, e.g., alcohol or drug carriers such as liposomes, can be used, with some success, to penetrate the stratum corneum. The barrier function of the skin presents a very significant problem to pharmaceutical manufacturers interested in topical administration of drugs or in cutaneous collection of bodily fluids.

Electrosurgery is a method whereby tissue coagulation and/or dissection can be effected. In electrosurgery, radiofrequency (RF) current is applied to tissue by an active electrode. In a bipolar system, the current is passed through tissue between two electrodes on the same surgical instrument, such as a forceps. In a monopolar system, a return-path (ground) electrode is affixed in intimate electrical contact with some part of the patient. Because of the importance of the ground electrode providing the lowest impedance conductive path for the electrical current, protection circuits monitoring the contact of the ground with the patient are often employed wherein an increase in ground electrode-skin impedance results in the instrument shutting down. A desired alteration in the tissue, usually coagulation or cutting, can be made by manipulating the treatment electrode shape, the electrode position (contact or non-contact) with respect to the tissue surface, frequency and modulation of the radiofrequency current, power of the radiofrequency current and the length of time for which it is applied to the tissue surface, and peak-to-peak voltage of the radiofrequency current with respect to the tissue type.

For example, decreasing electrode size translates into increased current density in the tissue proximal to the electrode and so a more invasive tissue effect, such as dissection as compared to coagulation, is realized. Similarly, if the electrode is held close to the tissue but not in contact, then the area of radiofrequency-tissue interaction is smaller as compared to the area when the electrode is in contact with the tissue, therefore, the effect on the tissue is more invasive. By changing the waveform of the applied radiofrequency current from a continuous sinusoid to packets of higher peak voltage sinusoids separated by dead time (for example, with a duty cycle of 6%), then the tissue effect can be changed from dissection to coagulation. Increasing the voltage of the waveform increases the invasiveness of the tissue effect, and the longer the tissue is exposed to the radiofrequency, the greater the tissue effect. Finally, different tissues respond to radiofrequency differently because of their different electrical conductive properties, concentration of current carrying ions, and different thermal properties. In a typical electrosurgical system, radiofrequency frequencies of 300 kHz to 4 MHz are used since nerve and muscle stimulation cease at frequencies beyond 100 kHz.

Devices incorporating radiofrequency electrodes for use in electrosurgical and electrocautery techniques are described in Rand[1] et al. and U.S. Pat. Nos. 5,281,216; 4,943,290; 4,936, 301; 4,593,691; 4,228,800; and 4,202,337. U.S. Pat. Nos. 4,943,290 and 4,036,301 describe methods for injecting nonconducting liquid over the tip of a monopolar electrosurgical electrode to electrically isolate the electrode, while energized, from a surrounding electrically conducting irrigant. U.S. Pat. Nos. 5,195,959 and 4,674,499 describe monopolar and bipolar electrosurgical devices, respectively, that include a conduit for irrigating the surgical site.

U.S. Pat. Nos. 5,217,455, 5,423,803, 5,102,410, 5,282, 797, 5,290,273, 5,304,170, 5,312,395, 5,336,217 describe laser treatment methods for removing abnormal skin cells, such as pigmentations, lesions, soft tissue and the like. U.S. Pat. Nos. 5,445,634 and 5,370,642 describe methods for using laser energy to divide, incise or resect tissue during cosmetic surgery. U.S. Pat. No. 5,261,410 is directed to a method and apparatus for detecting and removing malignant tumor tissue.

U.S. Pat. Nos. 5,380,316, 4,658,817, 5,389,096, International Publication WO 94/14383 and European Patent Application No. 0515867 describe methods and apparatus for percutaneous myocardial revascularization. These methods and apparatus involve directing laser energy against the heart tissue to form transverse channels through the myocardium to increase blood flow from the ventricular cavity to the myocardium. Devices and methods in U.S. Pat. Nos. 5,683,366, 5,697,536, 6,228,078, and 5,888,198 describe bipolar and monopolar radiofrequency electrosurgical devices that use a method of tissue disintegration as a means to ablate tissue prior to myocardial revascularization, tissue resurfacing or other surgical procedures.

Devices and methods for drug delivery using laser ablation systems have been described. U.S. Pat. No. 6,251,100 provides an improved method of administering a pharmaceutical composition, such as an anesthetic through the skin of a patient without the use of a sharp or needle. This method includes the step of irradiating the stratum corneum of a region of the skin of the patient using a laser. By a selection of parameters, the laser irradiates the surface of the skin precisely to a selectable depth, without causing clinically relevant damage to healthy proximal tissue. A pharmaceutical composition is then applied to the region of irradiation. International Publication WO 00/57951 describes the use of non-ionizing energy, including lasers, to improve methods of administering pharmaceuticals in tissues, including the skin. In the case of RF energy, certain applications describe feedback mechanisms that are used to prevent damage to viable tissue in the area surrounding the treatment site including U.S. Patent Publication No. 2002/0010414 A1 and WO 01/21068.

It is notable that consistent means of treatment are desirable. The Code of Federal Regulations (21 CFR 860.7(e)(1)) establishes that there is "reasonable assurance that a device is effective when it can be determined, based upon valid scientific evidence, that in a significant portion of the target population, the use of the device . . . will provide clinically significant results." Devices that cannot be shown to provide consistent results between patients, or even within a patient upon multiple use, will have minimal utility and may not be approvable for broad use.

Beyond devices, it is generally desirable to develop medical products with critical controls that can deliver a precise result. Of critical concern is the delivery of many types of drugs. Certain drugs can be described as having a "broad" or "narrow" therapeutic index (TI). That is, some drugs may be useful over a broad range of concentrations (broad TI), and thus are safe for the general population, while other drugs may only be effective over a narrow concentration range (narrow TI) and may even be dangerous when administered in greater than recommended concentrations. This is particularly true where a drug has a narrow therapeutic index; the delivery of the drug must be controlled carefully so as to avoid potentially harmful effects.

The FDA in its PMA Memorandum #P91-1: Clinical Utility and Premarket Approval has established that devices that cannot be controlled may have limited utility. Particularly a drug delivery device may have limited utility if no assurance can be made that a consistent dosage is delivered throughout the patient population. The drug-device combination must be capable of consistently delivering a dosage. As part of INDs and NDAs for administered drug products, bioavailability studies focus on determining the process by which a drug is released from the oral dosage form and moves to the site of action.

Bioavailability data provide an estimate of the fraction of the drug absorbed, as well as the drug's subsequent distribution and elimination. Bioavailability is defined in 21 CFR 320.1 as "the rate and extent to which the active ingredient or active moiety is absorbed from a drug product and becomes available at the site of action. For drug products that are not intended to be absorbed into the bloodstream, bioavailability may be assessed by measurements intended to reflect the rate and extent to which the active ingredient or active moiety becomes available at the site of action." This definition focuses on the processes by which the active ingredients or moieties are released from a dosage form and move to the site of action. A delivery device which does not consistently release the same levels of a drug product due to the design of a product will have limited clinical utility as there can be no assurance that a certain dosage has been delivered at any point in time.

Furthermore, studies to establish bioequivalence between two products are important to demonstrated safety and therapeutic efficacy in a product and will be a benchmark for approval of drugs by regulatory bodies. Bioequivalence is defined at 21 CFR 320.1 as "the absence of a significant difference in the rate and extent to which the active ingredient or active moiety in pharmaceutical equivalents or pharmaceutical alternatives becomes available at the site of drug action when administered at the same molar dose under similar conditions in an appropriately designed study." As noted in the statutory definitions, both bioequivalence and product quality bioavailability focus on the release of a drug substance from a drug product and subsequent absorption into the systemic circulation. Where the test product generates variable effect at the site of action, as compared to those of the reference product, the product cannot be claimed as consistent, will not have great clinical utility and could be dangerous to use.

Control of delivery for transdermal applications is achieved by delivering a fraction of what is "absorbable," and either regulating the size of the dosage or the amount that is released from the vehicle. The condition of the skin and its hydration are significant factors in the percutaneous absorption of drugs. Some solubility of the substance in both lipid and water is thought to be essential. The aqueous solubility of a drug determines the concentration presented to the absorption site and the partition coefficient strongly influences the rate of absorption across the absorption site (Pharmaceutical Dosage Forms and Drug Delivery Systems, Ansel, H. C., Popovich, N. G. Allen, L. V. Eds., Williams & Wilkins, Baltimore, 1995.) Vehicles that increase the hydration of the skin generally favor percutaneous absorption of drugs.

The inventors have recognized a need in the art for a device and improved methods of controllably facilitating permeation of substances across tissue membranes. Whereas mechanisms are published for protecting viable tissue surrounding the treatment site, the prior art is deficient in methods to achieve control over the alteration event in order to achieve variable rates of permeability. Specifically, the use of energy to alter the permeability of a biological membrane to a pharmaceutical or other biological molecule has been reported, however, the literature is deficient in reports of methods for controlling the treatment process in order to achieve a desired state of permeability.

SUMMARY OF THE INVENTION

One embodiment of the present invention provides a device—for altering a biological membrane in an individual comprising a means for delivering energy to the surface of the biological membrane; a means for monitoring a physiological state of the biological membrane during delivery of the energy; a means for modulating delivery of the energy to the biological membrane where the modulating is in response to a change in the monitored physiological state; and a housing means for the device.

Another embodiment of the present invention provides a method to control alteration of a biological membrane in an individual comprising the steps of contacting the biological membrane with the device disclosed herein; delivering energy to the biological membrane where the energy alters the biological membrane; monitoring the physiological state of the biological membrane where the physiological state changes as the biological membrane is altered; applying an algorithm to evaluate the change in the physiological state; modulating the energy delivery to the biological membrane in response to the value obtained for the physiological state thereby controlling the alteration of the biological membrane in the individual.

Yet another embodiment of the present invention provides a device for controlling the permeation of a substance across a biological membrane in an individual comprising a means for delivering energy to at least one surface area of the biological membrane, the energy causing an alteration in the area(s) of the biological membrane; a means for monitoring a physiological state of the biological membrane during delivery of the energy; and a means for modulating delivery of the energy to the surface area(s) of the biological membrane where the modulating is in response to a change in the monitored physiological state.

Still another embodiment of the present invention provides a method to control the permeation of a substance across a biological membrane in an individual comprising the steps of contacting the biological membrane with the device disclosed herein; delivering energy to at least one surface area on the biological membrane where the energy alters the biological membrane; monitoring the physiological state of the biological membrane where the physiological state changes as the biological membrane is altered; applying an algorithm to evaluate the change in the physiological state; modulating the energy delivery to the biological membrane in response to the value obtained for the physiological state where the degree of alteration of the biological membrane is dependent on the energy delivered to the surface area of the biological membrane; and delivering the substance to the surface area on the altered biological membrane where controlling the degree of alteration of the biological membrane thereby controls the permeation of the substance across the biological membrane.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
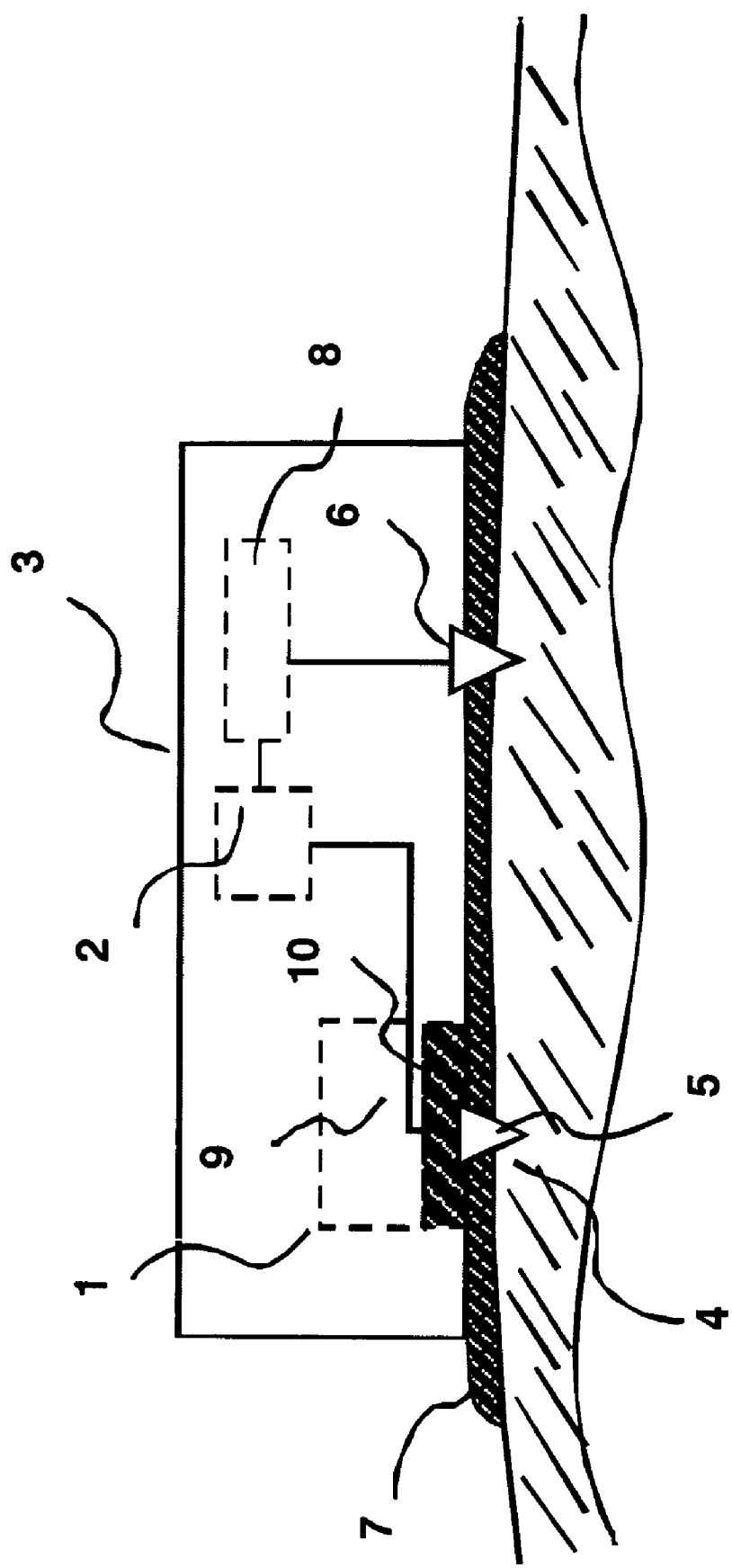
FIG. 1 is a schematic of a device that measures the condition of the target site, delivers energy to alter or ablate a membrane and adjusts the continued treatment according to feedback dependent on the condition of the site.

One embodiment of the present invention provides a device—for altering a biological membrane in an individual comprising a means for delivering energy to the surface of the biological membrane; a means for monitoring a physiological state of the biological membrane during delivery of the energy; a means for modulating delivery of the energy to the biological membrane where the modulating is in response to a change in the monitored physiological state; and a housing means for the device.

In an aspect of this embodiment, the means to delivery the energy comprises an energy delivery system; at least one first active electrode in electrical contact with a treatment site on the biological membrane; and a second return electrode distal to the first electrode and in electrical contact with the biological membrane. The delivery means may also have an electrically conductive fluid interface between the first electrode and the biological membrane or between the first and second electrodes and the biological membrane. The device may be in a patch or a probe. One example of the patch has a reservoir to contain a substance and an optional permeable membrane located between the reservoir and the biological membrane. The permeable membrane is in contact with the biological membrane or in contact with the electrically conductive fluid interface. An example of the substance contained in the reservoir is a pharmaceutical compound.

Furthermore, in this aspect of this embodiment the device has a monitoring means comprising a controller where the controller monitors a current flow between the first electrode(s) and the second electrode such that a change in the current flow corresponds to the change in the physiological state of the biological membrane. Optionally, the electrodes may form a galvanic cell.

Continuing with this aspect of this embodiment, the means to modulate the energy delivery is a microprocessor which is operably connected to a controller and to the energy delivery system. The microprocessor modulates the energy delivery from the energy delivery system to at least one first electrode in response to the change in the current flow between the first electrode and the second electrode distal to the first electrode. The current flow, monitored by the controller, corresponds to the change in the physiological state of the biological membrane.

In all aspects of this embodiment the biological membrane may be altered by ablating at least a portion of the membrane. An example of the biological membrane may be the stratum corneum. Representative examples of the energy delivered are radiofrequency energy, electrical energy or mechanical energy. The physiological states monitored may be an electrical property or a chemical property of the biological membrane. Examples of electrical properties and physiological states are impedance, conductivity or hydration.

Another embodiment of the present invention provides a method to control alteration of a biological membrane in an individual comprising the steps of contacting the biological membrane with the device disclosed herein; delivering energy to the biological membrane where the energy alters the biological membrane; monitoring the physiological state of the biological membrane where the physiological state changes as the biological membrane is altered; applying an algorithm to evaluate the change in the physiological state; modulating the energy delivery to the biological membrane in response to the value obtained for the physiological state thereby controlling the alteration of the biological membrane in the individual.

In an aspect of this embodiment the original value obtained for the physiological state prior to treatment is a control value that is compared to subsequently obtained values for the physiological state. These control values of the physiological state may be obtained from the same individual or from within a group of individuals. All other aspects of this embodiment such as the device, the biological membrane, the physiological states monitored and substances are as disclosed supra.

Yet another embodiment of the present invention provides a device for controlling the permeation of a substance across a biological membrane in an individual comprising a means for delivering energy to at least one surface area of the biological membrane where the energy causes an alteration in the area(s) of the biological membrane; a means for monitoring a physiological state of the biological membrane during delivery of the energy; and a means for modulating delivery of the energy to the surface area(s) of the biological membrane where the modulating is in response to a change in the monitored physiological state.

In this embodiment the energy delivery system has at least one first active electrode in electrical contact with the surface area on the biological membrane and a second return electrode distal to the first electrode and in electrical contact with the biological membrane. The energy delivery means may comprise an electrically conductive fluid interface as disclosed supra. The first electrode(s) may be in a patch or at least one probe. In one aspect the probe(s) may be moved over the surface of the biological membrane. In another aspect the patch may comprise a reservoir and permeable membrane as disclosed supra. Further in this embodiment the means to monitor the physiological state in the biological membrane and the means to modulate energy delivery to the biological membrane are as disclosed supra.

In all aspects of this embodiment the surface area may be from about one centimeter squared to about twenty centimeters squared. All other aspects of this embodiment such as the device, the biological membrane, the physiological states monitored and substances are as disclosed supra.

Still another embodiment of the present invention provides a method to control the permeation of a substance across a biological membrane in an individual comprising the steps of contacting the biological membrane with the device disclosed herein; delivering energy to at least one surface area on the biological membrane where the energy alters the biological membrane; monitoring the physiological state of the biological membrane where the physiological state changes as the biological membrane is altered; applying an algorithm to evaluate the change in the physiological state; modulating the energy delivery to the biological membrane in response to the value obtained for the physiological state where the degree of alteration of the biological membrane is dependent on the energy delivered to the surface area of the biological membrane; and delivering the substance to the surface area on the altered biological membrane where controlling the degree of alteration of the biological membrane thereby controls the permeation of the substance across the biological membrane.

In an aspect of this embodiment the permeation of the substance is further controlled by increasing the total surface area on the biological membrane. The total surface area can be one continuous area on the biological membrane or can be an increase in the number of discrete surface areas on the biological membrane. Again, all other aspects of this embodiment such as aspects of the method, aspects of the device, the biological membrane, the physiological states monitored and substances are as disclosed supra.

The present invention provides a device and methods for improving the permeability of the skin or other biological membranes to certain substances. Targets associated with tissue interfaces are made permeable to diagnostic and therapeutic substances. The device and methods disclosed herein can improve the permeation rate of pharmaceuticals across a biological membrane into an individual or can increase the diffusion of substances out of a tissue of the individual.

The system allows the operator to cause molecular alterations in necrotic tissue or dead cells present in, for example, the stratum corneum by selectively applying energy, e.g., electromagnetic energy such as radiofrequency energy, laser energy, mechanical energy or heat energy, to the skin in the presence of a desired substance prior to its application or prior to withdrawal of compounds from the tissues. The transient or sustained molecular alteration of membranes and tissue interfaces induced by high frequency electromagnetic energy or by the physical products of the interaction of the electromagnetic energy and matter improve permeability to the particular substance. The system is useful for delivery of drugs, diagnostic agents and for extraction of blood chemicals and gases for diagnostics.

The devices described herein can be used to reduce the stratum corneum in order to create a site which is substantially more permeable to substances, including drugs and other medically useful compounds. As successive layers of the stratum corneum are removed, permeation generally increases until a maximum rate of permeation or flux occurs at which point the stratum corneum is completely removed. Thus, by manipulating the depth or degree of reduction, one may control the flux of a certain substance.

Additionally, an advantage of the present method of transcutaneous drug delivery, particularly over previous methods involving lasers, is that the high frequency voltage can be continuously or intermittently applied to the target site to reduce the stratum corneum. Thus, the site can be treated over long periods of time, thereby slowing or stopping the healing process that would otherwise replace the stratum corneum. Intermittent pulses can be delivered as the layers are replaced, thereby maintaining the increased permeability at the site.

The device has a control means. Current flow from at least two electrodes that are in electrical contact with the biological membrane at the target site or in contact with an electrically conductive fluid at an interface with the biological membrane is controlled based on impedance between the electrode terminals at the target site and that of the return electrode. Alternatively, the control is mediated through the creation of a galvanic cell whereby two electrodes used in combination are composed of dissimilar metals and electrical charges are allowed to migrate between them via an electrolyte defined as body fluid present below the surface of the skin.

As the successive layers of stratum corneum are removed, the probes encounter a hydration gradient, which results in increased conductance. This last method may optionally require the probe to be in contact with the skin. Again, optionally, contact with a liquid interface at the skin surface would minimize the effect of contaminants in the area that may have an insulative effect. The information on conductance is then relayed to a controller, which in turn adjusts the treatment of the target site to achieve a desired alteration (or ablation). The control means can consist of a means to measure the change in the charge storage characteristics of the skin, such that increasing "leakiness" to ions and/or charge, due to breakdown of the "skin battery" is an indication of the depth of treatment.

An additional control means consists of a means to measure the change in the degree of hydration at the target site, whereby increasing hydration is an indication of the depth of treatment. In turn, the degree of hydration is an indication of the likely permeability of a substance through the membrane. The degree of hydration may be determined by corneometry or, preferably, by evaluation of conductance which becomes more efficient as increasing hydration is encountered. A feedback loop is caused by the information on hydration being monitored by a central controller which uses an algorithm to compute relative or absolute hydration. The controller then signals the device to continue or cease the treatment process, in order to seek the optimal depth of treatment with respect to hydration and permeability characteristics of a particular substance.

Furthermore, monitoring the depth of treatment, through feedback modulation or by measuring physical parameters in the treatment site itself, also may include, but not be limited to, electrical properties of the membrane, for example its charge storage characteristics, electrical and physiological impulses pulses generated by the heartbeat (ECG), and ionic properties, whereby the treatment cycle may be interrupted when a desired endpoint is reached. When these parameters are measured, they may be compared to measurements taken prior to treatment, or may be compared to a database of values collected from an appropriate population.

Once the barrier is reduced, a drug may be supplied to the surface of the target. Alternatively, the drug may be supplied in the electrically conductive liquid during the ablation process or the drug may be supplied from a reservoir independent of the electrically conductive liquid and applied after the process of ablation occurs. An advantage to this device and this method is that the ablation process occurs at a relatively low temperature, thus minimizing damage to surrounding tissue or to the drug itself.

The present invention can greatly accelerate the rate of percutaneous absorption. The device alters the stratum corneum in a manner that exposes increasingly hydrated layers of this skin layer, thereby increasing the percutaneous absorption of a substance through this layer. Further, the device seeks a pre-determined state of hydration, using this as a benchmark for standardizing permeability of a substance. Thus, consistent reliable dosages are delivered or a consistent amount of material is collected between sites and across a patient population by adjusting the permeability characteristics of the treatment site itself, in addition to traditional methods in the formulation The present method can be used for transport of a variety of systemically or locally acting pharmaceutical substances. For example, these substances may be nitroglycerin and antinauseants such as scopolamine, antibiotics such as tetracycline, streptomycin, sulfa drugs, kanamycin, neomycin, penicillin, or chloramphenicol. Various hormones such as parathyroid hormone, growth hormone, gonadotropins, insulin, ACTH, somatostatin, prolactin, placental lactogen, melanocyte stimulating hormone, thyrotropin, parathyroid hormone, calcitonin, enkephalin, or angiotensin, steroidal or non-steroidal anti-inflammatory agents, and systemic antibiotic, antiviral or antifungal agents may also be transported. Furthermore, the substances of the present invention may be interstitial fluid or a diagnostic reagent. For example, interstitial fluid could be used to measure analytes. These substances may be removed from tissue using the methods disclosed herein.

As described below, the invention provides a number of therapeutic advantages and uses, however such advantages and uses are not limited by such description.
The Device
General Features The device may be in a patch or in a probe form. An active electrode may be placed in proximity to the target tissue site and a return electrode may be positioned distal from the first electrode so a current flow path is generated between the two electrodes when a high frequency power source is applied. The active electrode may have a transducer or may comprise an electrode array having a plurality of isolated electrode terminals. The power source may be distal or integral to the unit. Either one or both electrodes may optionally be placed within an electrically conducting liquid, such as isotonic saline.

Voltage may be applied between the active and the return electrode through the current flow path created by the electrically conducting liquid in either a bipolar or monopolar manner. Preferably, the current flow path may be created in the system between the patch or probe and the skin whereby the target site and return electrode are bathed in an electrically conductive solution. Alternatively, the probe may be scanned across an area of the skin to expand the area useful for treatment or across the patch designed to encompass a large surface area. In both cases, the return electrode is spaced from the active electrode and shielded by an insulating material, thus reducing the risk of exposure of the return electrode to nearby tissue.

The voltage is believed to result in the formation of a high intensity electric field which is generated at the distal end of the active electrode where the fluid is supplied to the target site, which in turn generates a high energy plasma of electrons and, possibly, photons, which vaporize or alter the adjacent dead or necrotic cells. Precise control over the process results from manipulation of the voltage, i.e., voltage, frequency, duty cycle, pulse-width, pulse shape, with respect to changes, for example, in the conductance across the target site.

The device may be optionally controlled with a feedback device that monitors the impedance of the target allowing for automated control based on the variance in the impedance. The device may be further controlled through the continual or intermittent supply of the electrically conductive fluid. This continued or intermittent treatment ensures that the site of treatment is maintained at the more permeable state.
Safety Interlock A safety interlock may be affixed to the distal end of the active electrode, or integrated into the patch such that the device cannot be utilized unless the interlock is engaged, and only under proper use. For example, the interlock could be mechanical, electrical or optical. In the "on" position (engaged or disengaged), the device may be operational. In the "off" position, the device would fail to be operational.
Container A container may be attached to the distal end of the active electrode such as to contain the spark and collect ablated tissue. The container may be permanent or disposable. Alternatively, in a patch device, the container would be equivalent to a disposable or non-disposable component that is in contact with the skin. The container may be modified to hold, or receive through an opening, a pharmaceutical or other substance, which may then be delivered simultaneously, or shortly after irradiation occurs. The container may be integral to, or function independently of a safety interlock.
Use of the Device
Control Over Delivery of Pharmaceuticals In general, the impedance of the skin can approach values as high as $10^8$ ohms·cm$^2$. As successive layers of the stratum corneum are removed, this impedance can drop to a fraction of that value. This drop in impedance can be monitored as a measure of the degree of the process. Another aspect of the invention is that, with the other parameters set, the depth of treatment can be precisely controlled by continuously monitoring the impedance across the target area, and causing a feedback loop whereby the process is halted when a desired endpoint is met. Therefore, various settings on the device can be adjusted to allow successive reduction of the stratum corneum.

This method of delivering a pharmaceutical creates a variable size zone in which the target is irradiated, and minimizes the risk of thermal necrosis on tissues surrounding the target site. A practical round irradiation site can range from 0.1-5.0 cm in diameter. After irradiation, the drug can then be applied directly to the skin or in a pharmaceutically acceptable formulation such as a cream, ointment, lotion or patch. One of ordinary skill in the art would have no trouble in determining how to formulate the drug for this topical application.

Alternatively, the delivery zone can be enlarged by strategic location of the irradiation sites and by the use of multiple sites. For example, in the case of an anesthetic, a region of the skin may be anesthetized by first scanning the desired area with the active electrode such that the treatment occurs over a larger surface area. Or, a patch device can incorporate a single large transducer or multiple transducer, i.e., electrodes, such that the surface area of treatment can be quite large. An important advantage of the device and method is that the size of the treatment site can be conveniently modulated. Further, the size and shape of the treatment site may be altered through the use of multiple probes or through the size and shape of the probes.

Control by Measuring State of Hydration

An object of the invention is to cause a feedback loop in an energy delivery device that identifies a particular hydration level in a membrane at which level a substance may have improved permeability. The devices described are preferably used for alteration or ablation of a membrane, usually the stratum corneum of the skin, whereby the alteration or ablation results in increased permeability to substances. In one instance the device senses a particular state of hydration which corresponds to increased permeability of a particular substance. When an optimal threshold of hydration is reached the energy delivery is reduced or curtailed.

Change in Conductivity

One embodiment of the invention includes an electrode present at the treatment site and a second electrode distal to the treatment site. As energy is delivered to the treatment site, successive layers of the membrane, preferably the stratum corneum, at the treatment site are removed. This removal results in improved conductance in the circuit formed between the two electrodes as increasing hydration is encountered. Feedback of information regarding this change in hydration to a central controller may then result in the controller modulating the output of the energy device in response to the change. The controller monitors the change in conductance until a desired level is reached and then terminates the procedure.

Control by Creation of Galvanic Cell

A further embodiment of the invention creates a galvanic cell between two monitoring electrodes and fluids encountered in the membrane as a result of treatment. The galvanic cell comprises a tip, which is placed adjacent the ablation site on the tissue, in combination with an electrically conducting dissimilar metal plate which is in contact with the tissue at a location remote from the ablation site and an electrolyte defined by the intervening tissue. A galvanic cell is created when the tip and the plate have different work functions because of migration of electrical charges there between. When alteration or ablation at the treatment site occurs, charges generated by an electrochemical gradient between the electrodes begin to migrate. This migration of charges is increasingly efficient as the hydration level increases. Thus, the functionality of the galvanic cell may be monitored as a means to detect changes in hydration and the information used to regulate the energy output of the device.

Control of Toxicity of Pharmaceuticals

One of the limitations of transcutaneous delivery of drug formulations is that the drug can be toxic at high doses and, therefore, must be modulated to permeate the skin at a controlled rate. In the present case modulation may occur by limiting the depth of the treatment and by controlling the flux of the drug by delivering it over a larger surface area.

It is therefore a further object of the invention to provide a large surface area, e.g., greater than 1 cm$^2$, for the delivery of pharmaceutically active substances where those substances may adversely interact with tissues. Further, substances which have poor permeability characteristics, even in the presence of an altered or ablated membrane, may be better delivered through a larger surface area. Treatment areas as large as 20 cm$^2$ may be created using the devices described herein.

Depth of the treatment is correlated with the change in electrical properties across the treatment site as the stratum corneum is reduced. When a desired depth is reached, the device can be shut down. Also, the skin hydration can be used to modulate the electromagnetic energy in such a way that the process becomes curtailed as the hydration detected is of a certain predetermined value. Additionally, this defines a means by which the flux of permeation of a particular substance may be modulated through variations in the surface area and depth of the treatment site.

The present invention provides a means for treating local pain or infections or for applying a substance directly to a small specified area thus eliminating the need to provide high, potentially toxic amounts systemically through oral or intravenous administration. Locally acting pharmaceuticals such as alprostadil (for example, Caverject™ from Pharmacia & Upjohn), various antibiotics, antiviral or antifungal agents, or chemotherapy or anti-cancer agents, can be delivered using this method to treat regions proximal to the delivery site. Protein or DNA based biopharmaceutical agents can also be delivered using this method.

Delivery of Immunogens

Antigens derived from a virus, bacteria or other agent which stimulates an immune response can be administered through the skin for immunization purposes. The antigen is delivered through the outer layers of the stratum corneum, either singly or multiply, and the immunogen is provided in an appropriate formulation. For booster immunizations, where delivery over a period of time increases the immune response, the immunogen can be provided in a formulation that penetrates slowly through the treatment site, but at a rate faster than possible through unaltered skin.

Delivery of Anti-Inflammatory Drugs

Analgesics and other non-steroidal anti-inflammatory agents, as well as steroidal anti-inflammatory agents, may be caused to permeate through reduced stratum corneum to locally affect tissue within proximity of the irradiated site. For example, anti-inflammatory agents such as Indocin™ (Merck & Co.), a non-steroidal drug, are effective agents for treatment of rheumatoid arthritis when taken orally, yet sometimes debilitating gastrointestinal effects can occur. By administering such agents through alteration sites, these potentially dangerous gastrointestinal complications may be avoided. Furthermore, high local concentrations of the agents may be achieved more readily near the site of irradiation as opposed to the systemic concentrations achieved when orally administered.

Drawing Fluids, Gases or Other Biomolecules

The devices provided herein can be used to alter the stratum corneum to improve the collection of fluids, gases or other biomolecules through the skin. The fluid, gas or other biomolecule can be used for a wide variety of tests. For example, the technique of the present invention may be used to improve the ability to sample extracellular fluid in order to quantify glucose or other analytes. Glucose is present in the extracellular fluid in the same concentration as, or in a known proportion to, the glucose level in blood.

Alteration without Ablation

The technique of successive removal of layers of dead or necrotic cells of the stratum corneum provides several advantages. Preferably, the stratum corneum is reduced, but not removed, so that its structural and biochemical makeup still permit drugs to permeate. Therefore, the skin after irradiation still presents a barrier, albeit reduced, to external factors such as viruses and chemical toxins. Less energy is required for reduction than is required to entirely remove the stratum corneum, thus smaller and cheaper devices can be used. The technique also minimizes the damage to surrounding tissues providing a more rapid and efficient replacement of the stratum corneum.

Embodiments of the present invention are better illustrated with reference to the Figure(s), however, such reference is not meant to limit the present invention in any fashion. The embodiments and variations described in detail herein are to be interpreted by the appended claims and equivalents thereof.

An embodiment of the device is shown in FIG. 1. The device contains a patch 1 and an energy delivery system 2 integrated into a housing 3. The energy delivery system 2 is capable of delivering energy to a target site 4 on a biological membrane 7 resulting in an ablation or alteration of the membrane. At least one electrode 5 is in electrical contact with the ablation site 4. This contact may optionally involve a fluid interface 8 that improves the flow of charges between the electrode surface 5 and the treatment site 4. A second electrode 6 may be located distally from the first electrode 5 such that the biological membrane 7 forms a bridge between the electrodes 5,6 which may be composed of similar or different materials. A microprocessor (not shown) present in a controller 9 generates a current across the electrodes 5,6. Alternatively, the two electrodes 5,6 form a galvanic cell that distributes a current based on the migration of ions between them. The controller 9 detects changes in the condition of the treatment site 4 and, according to an algorithm, sends a signal to the energy delivery system 2 to continue or cease the delivery of energy until a certain predetermined condition of the treatment site 4 is reached. A patch 1 housed within the system 3 contains a substance 11 held in a reservoir 10 to be delivered to the target site. In one form of the device, a permeable membrane 12 modulates the release of the substance 11 to the treated site 4.

Any patents or publications mentioned in this specification are indicative of the levels of those skilled in the art to which the invention pertains. These patents and publications are herein incorporated by reference to the same extent as if each individual publication was incorporated specifically and individually by reference. One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:

1. A device for altering a biological membrane, wherein the biological membrane is the stratum corneum, in an individual comprising:
   an energy delivery system;
   one or more first active electrodes operably connected to the energy delivery system and in electrical contact with a treatment site on the biological membrane; and
   a second return electrode distal to the first electrode(s) and in electrical contact with the biological membrane;
   a controller configured to monitor a change in current flow between the first electrode(s) and the second electrode, said change in current flow corresponding to a change in a physiological state of the biological membrane; and
   a microprocessor operably connected to the controller and to the energy delivery system and configured to modulate energy delivery from the energy delivery system to at least one first electrode in response to the change in current flow between the first electrode(s) and the second electrode.

2. The device of claim 1, further comprising a housing.

3. The device of claim 1, further comprising an electrically conductive fluid interface between the first electrode and the biological membrane or between said first and second electrodes and said biological membrane.

4. The device of claim 1, further comprising a patch or one or more probes containing the first electrode(s).

5. The device of claim 4, wherein said patch further comprises:
   a reservoir to contain a substance; and
   an optional permeable membrane located between said reservoir and said biological membrane, wherein said permeable membrane is in contact with said biological membrane or in contact with an electrically conductive fluid on said biological membrane.

6. The device of claim 5, wherein said substance is a pharmaceutical compound.

7. The device of claim 1, wherein the first electrode and the second electrode form a galvanic cell.

8. The device of claim 7, wherein the first electrode and the second electrode are composed of electrically conducting dissimilar metals.

9. The device of claim 1, wherein the energy is radiofrequency electromagnetic energy, electrical energy or mechanical energy.

10. The device of claim 1, wherein the physiological state is an electrical property or a chemical property of the biological membrane.

11. The device of claim 1, wherein the physiological state is hydration.

12. A method to control alteration of a biological membrane, wherein the biological membrane is the stratum corneum, in an individual comprising the steps of:
   contacting said biological membrane with the device of claim 1;
   delivering energy to said biological membrane; wherein said energy alters said biological membrane;
   monitoring the change of the physiological state as the membrane is altered;
   applying an algorithm to obtain a value corresponding to the change in physiological state;
   modulating energy delivery to the biological membrane in response to said value obtained; thereby controlling the alteration of the biological membrane in the individual.

13. The method of claim 12, further comprising:
   comparing the value obtained for the change in physiological state to a control value for the physiological state obtained prior to energy delivery.

14. The method of claim 13, wherein said control value is obtained from the same individual or within a group of individuals.

15. The method of claim 12, wherein the first electrode(s) are contained within a patch that further comprises a reservoir containing a pharmaceutical substance, the method further comprising modulating permeation flux of the pharmaceutical substance from the reservoir through the altered biological membrane based on the obtained value for the physiological state.

16. The method of claim 15, wherein the patch further comprises a permeable membrane located between the reservoir and the biological membrane, said permeable membrane contacting the biological membrane or contacting an electrically conductive fluid on the biological membrane.

17. The method of claim 12, wherein the first electrode(s) are contained within one or more probes, the method further comprising moving the probe(s) over one or more areas of interest on the biological membrane to increase a total altered surface area thereof.

* * * * *